(12) United States Patent
Carner

(10) Patent No.: US 6,253,111 B1
(45) Date of Patent: Jun. 26, 2001

(54) MULTI-CONDUCTOR LEAD

(75) Inventor: David J. Carner, Fremont, CA (US)

(73) Assignee: Pacesetter, Inc., Sylmar, CA (US)

( * ) Notice: Subject to any disclaimer, the term of this patent is extended or adjusted under 35 U.S.C. 154(b) by 0 days.

(21) Appl. No.: 09/298,244

(22) Filed: Apr. 23, 1999

Related U.S. Application Data

(63) Continuation-in-part of application No. 09/050,513, filed on Mar. 30, 1998, now abandoned.

(51) Int. Cl.[7] .................................................. A61N 1/05
(52) U.S. Cl. ............................ 607/122; 607/116; 600/373
(58) Field of Search ................................ 607/115, 116, 607/119, 122, 123, 725; 600/372–374, 377

(56) References Cited

U.S. PATENT DOCUMENTS

| | | |
|---|---|---|
| 3,416,533 | 12/1968 | Fisher et al. . |
| 3,788,329 | 1/1974 | Friedman . |
| 3,804,098 | 4/1974 | Friedman . |
| 4,499,907 * | 2/1985 | Kallok et al. .......................... 607/122 |
| 4,559,951 | 12/1985 | Dahl et al. . |
| 5,275,171 | 1/1994 | Barcel . |
| 5,324,326 * | 6/1994 | Lubin .................................... 607/122 |
| 5,330,522 | 7/1994 | Kreyenhagen . |
| 5,405,372 | 4/1995 | Gilljam et al. . |
| 5,466,253 | 11/1995 | Doan . |
| 5,628,778 | 5/1997 | Kruse et al. . |

* cited by examiner

Primary Examiner—George R. Evanisko

(57) ABSTRACT

The invention resides in a multi-conductor lead comprising an inner tube containing at least two lumens, the tubing having an outer surface defining an outer diameter thereof. Two coiled conductors are housed within the at least two lumens in the tubing and extend longitudinally therewithin. A third coiled conductor is disposed circumferentially about the outer surface of the tubing. Insulation coating is disposed circumferentially about the outer conductor. Accordingly, the outer coil serves to prevent subclavian crush from causing the inner conductors to short to each other.

11 Claims, 2 Drawing Sheets

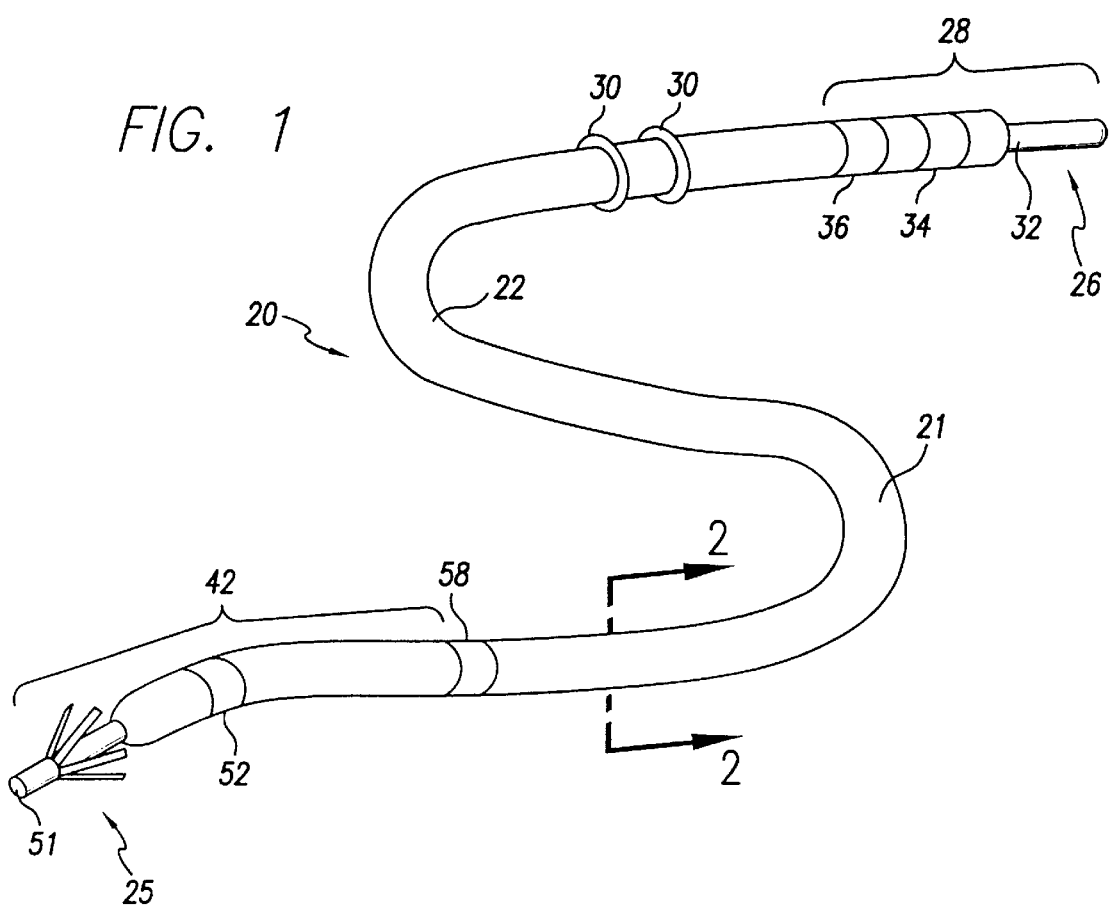
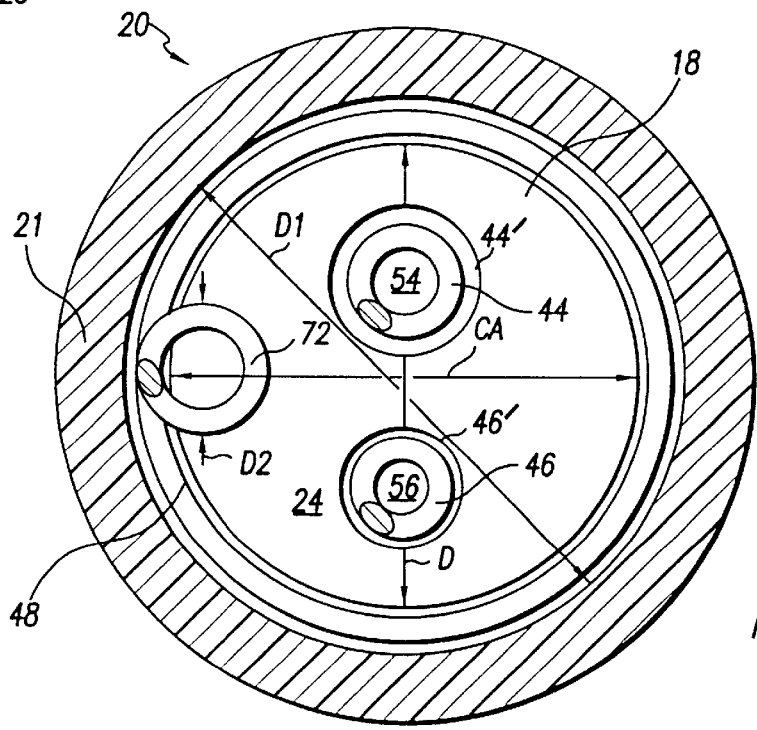

MULTI-CONDUCTOR LEAD

CROSS-REFERENCE TO RELATED APPLICATIONS

This application is a continuation-in-part of application Ser. No. 09/050,513, filed Mar. 30, 1998 now abandoned.

FIELD OF THE INVENTION

This invention relates generally to an implantable stimulation lead for use with a cardiac pacemaker, and more specifically, to an implantable stimulation lead having lead body wherein two or more inner conductors are protected from abrasion by a surrounding outer coil.

BACKGROUND OF THE INVENTION

It is known that leads used in cardiac stimulation are often implanted transvenously or transthoracically with the result that the lead body can be physically crushed by either bones (i.e. "first rib-clavicle") or by tissue (costoclavicular ligament complex, subclavius muscle) and by anchoring sleeves which are tied-down so tightly that the lead body can be crushed or damaged.

The result of these crushing or constrictive stresses, which are made more pronounced by movements of the patient, can become manifested by severe damage to the conductors, such as by abrasion of the insulation of the conductors within the lead body which, in turn, can result in failed conductors and/or failed insulation. This is because the conductors within the lead are usually disposed in close proximity to one another. For example, in a tripolar pacing lead, at least three conductors would be housed within the lead and must be maintained in a spatially disposed relationship with one another.

Conductor mechanical damage including fractures and/or insulation breaks may occur in about 2% to 3% of implanted leads. In patients who are not pacemaker dependent, a failure event is usually not life-threatening, but can require corrective procedures with potential for complications. Mechanical damage can occur as coil deformation, coil fracture, mechanically induced insulation breaches, and insulation wear observed individually or in combination.

SUMMARY OF THE INVENTION

The invention resides in a multi-conductor lead defined by an inner tube having at least two lumens formed therein. About the inner tube is a first coiled conductor, and within the at least two lumens are disposed a respective second and third conductor extending longitudinally therewith.

At the distal end, the first coiled conductor has a portion thereof which is offset wound at a diameter which is smaller than that of the diameter thereof which is coiled about the inner tube so that a connection can be made in-line with the sensor or distal electrode.

An advantage of this arrangement is to provide a multi-conductor lead body having a design which resists mechanical damage, in particular abrasion.

Another advantage is to provide a lead body of the aforementioned type wherein one of the conductors provides a mechanical barrier against the adverse effects of abrasion relative to the remaining conductors in the lead body.

Further, another advantage is to provide a lead body of the aforementioned type which includes a sensor which is capable of connecting to one or more conductors disposed within the tubing, while allowing one conductor to pass through to the distal tip electrode.

In the preferred embodiment, the multi-conductor lead has an inner tube extending concentrically along a central axis thereof, and containing at least two lumens therein. The inner tube has an outer surface defining an outer diameter thereof.

A first coiled conductor is provided and has a predetermined diameter which is slightly greater than the outer diameter of the tubing such that the first conductor is disposed circumferentially about the outer surface of the tubing. An insulation sheath is provided circumferentially about the first conductor.

A second and third conductor are disposed within the at least two lumens in the tubing so as to extend longitudinally therewithin.

At the distal end, the first conductor has an offset portion which is directed for connection to another element of the lead (e.g., a ring electrode or a sensor). Ideally, the first conductor's offset portion is a continual length of the first conductor and ends in a coil portion which has a diameter substantially less than the original diameter of the first conductor length.

In one embodiment of the invention, a sensor is disposed axially in line with the inner tube and has a first and second terminal associated with, and connected to, a selected two of the conductors. The remaining one of the conductors may be selected to pass beneath the sensor to the distal end of the lead body.

Ideally, the first outer conductor is a drawn-filled conductor. The drawn-filled conductor is preferably a silver core MP35N conductor used to reduce the resistance inherent to a large diameter conductor.

BRIEF DESCRIPTION OF THE DRAWINGS

FIG. 1 shows a perspective view of a lead body of the present invention;

FIG. 2 shows a sectional view along line 2—2 of FIG. 1;

DETAILED DESCRIPTION OF THE PREFERRED EMBODIMENT

Figure 3:
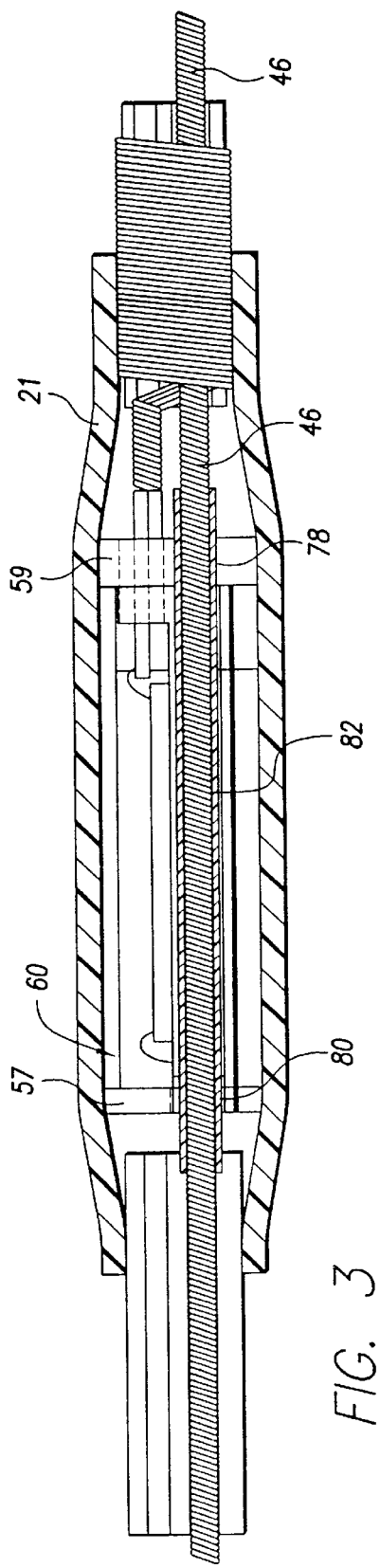
FIG. 3 shows a partially cross-sectional side view of the lead body.

FIG. 1 depicts a multilumen pacing lead 20 according to the present invention. While a three electrode lead is shown in FIG. 1, it will be abundantly apparent that the principles of the present invention can be adapted to any lead requiring three or more conductors, such as a lead incorporating a sensor with one or more pacing electrodes, a quadrapolar (i.e., 4 electrode) system, a single-pass lead having electrodes in the atrium, or a multi-site pacing electrode for use in the coronary sinus. Suffice it to say that these applications are all within the spirit of the invention, and that one of skill in the art can readily apply the principles taught herein to satisfy these applications.

As shown in FIG. 1, the multilumen pacing lead 20 has an elongated lead body 22, extending between a proximal end 26 and a distal end 25, which includes electrical conductors extending through lumens within a multilumen tubing (not shown). At a proximal end 26 of the pacing lead 20 is a connector assembly 28, which is provided with sealing rings 30 and electrical connectors 32, 34 and 36 for connection to a pulse generator.

The insulating portions of the connector assembly 28 which space apart the connectors 32, 34 and 36 may be fabricated from segments of multilumen tubing of silicone, rubber, polyurethane, or other suitable plastic. The electrical connectors 32, 34 and 36 are preferably fabricated of stainless steel or other suitable conductive material.

At the distal end 25 of the pacing lead 20 is an electrode assembly 42 which may include multiple electrodes or sensors, and which is intended to be implanted into the heart. A tip electrode 51 is located at the distal end 25 of the electrode assembly 42. Two ring electrodes 52 and 58 are shown proximal to the tip electrode 51. The ring electrode 52 may be used, for example, as a anode in a bipolar pacing system.

Alternatively, the electrodes 52 and 58 can be used as sensor electrodes to determine various parameters of cardiac activity, such as, atrial electrical activity, ventricular electrical activity, or to sense impedance changes to determine stroke volume, pre-ejection fraction, and respiratory rate. Monitoring of these parameters is beneficial for advanced pacing systems to allow the pacemaker to more effectively control cardiac activity.

As shown in FIG. 2, the pacing lead 20 includes a multilumen tubing 24 which has an outer diameter D defined by an outer surface 18. A first coiled conductor 48 is circumferentially disposed about the multilumen tubing 24 (i.e., the inner diameter of the first coiled conductor is slightly greater than the outer diameter of the tubing). The first coiled conductor 48 is, in turn, covered by an outer sheathing 21.

The first conductor 48 is formed as a coiled conductor, but has an inner diameter D1 substantially larger than that of the second and third conductors, 44 and 46, yet is only slightly smaller in size than the inner diameter of the outer sheathing 21 as defined by the cylindrical surface 18. The inner diameter D1 of the first conductor 48 is such that it is coiled about the outer surface 18 of the multilumen tubing 24. Thus, in the event that abrasion occurs through the outer sheathing 21 of the multilumen inner tube, the first conductor 48 would act to stop such abrasion without jeopardizing the second and third conductors, 44 and 46, disposed internally thereof. The first conductor 48 is preferably a (DFT) drawn-filled inner tube type conductor.

Both the multilumen tubing 24 and the outer sheathing 21 are preferably fabricated of silicon, rubber, polyurethane, or another suitable plastic material having the properties of biocompatibility, biostability and flexibility.

As illustrated in FIG. 2, the multilumen inner tube 24 is generally circular in transverse cross-section and is concentric about the central axis CA of the lead body 22. A first lumen 44' is disposed, for example, on one side of the central axis CA while a second lumen 46' is disposed, for example, on the other side of the central axis.

The multilumen tubing 24 includes a second conductor 44 and a third conductor 46 disposed within the lumens 44' and 46', respectively. The conductors 44 and 46 are helically wound electrical conductors, each conductor being separated by the interposed insulation material of the multilumen tubing 24.

Each conductor 44 and 46 is itself defined by a spiral winding resulting in a hollow central area 54, which allows the lead body 22 to remain quite flexible. Also, the hollow central area 54 accommodates insertion of a guide wire or stylet (not shown) which is relatively stiff and which allows the doctor to guide and control the implantation of the pacing lead 20.

In addition, it should be understood that each conductor 44 and 46 may preferably be made up of a plurality of filars contained in a bundle to provide redundancy while also retaining flexibility by reducing the cross-sectional thickness which would be required for a single conductor. The conductors 44 and 46 are standard MP35N conductors.

In the preferred embodiment, the diameter of the lead body is in the range of between about 1.50 mm and 3.50 mm and preferably about 2.5 mm. It is to be understood that the conductors appear solid in cross-section, which results from a tightly wound helix having many turns per inch. obviously, for helixes with fewer turns per inch, the cross-section would show portions of adjacent windings.

Figure 4:
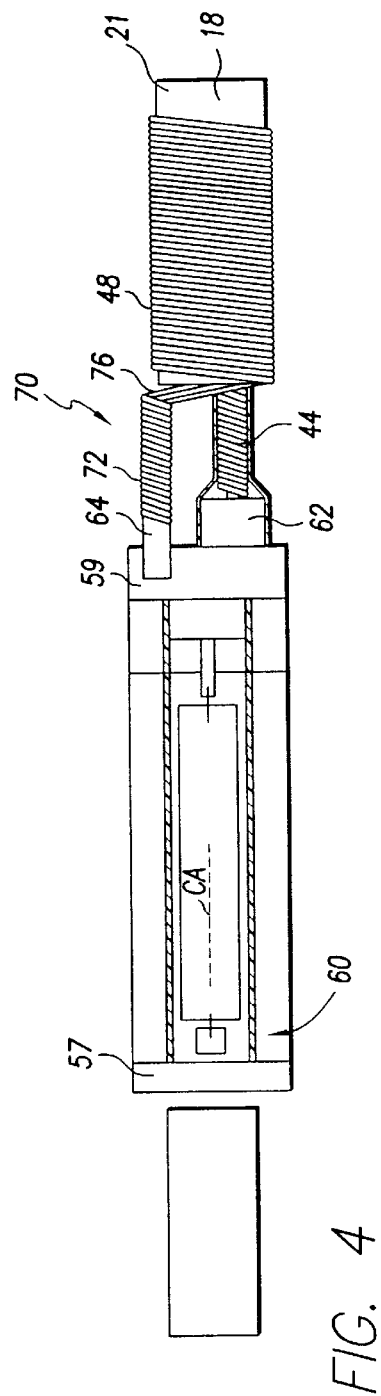
FIG. 4 shows a partially cross-sectional top view of the lead body.

FIGS. 3 and 4 illustrate two cross-sectional views of a sensor embodiment. It is recognized that ring electrodes, as shown in FIG. 1, could be substituted for the sensor terminals, and one of skill in the art could readily modify the present invention to achieve such configuration.

As seen in FIGS. 3 and 4, the lead body 20 includes a sensor device 60 which may be part of the electrode assembly 42 and is axially defined by a first end wall 57 and a second end wall 59. The sensor device 60 is axially connected at end wall 59 to one end of the multilumen tubing 24 as described below.

As illustrated in FIG. 4, the sensor 60 includes a first terminal 62 and a second terminal 64, each respectively associated with a selected one of the conductors 44, 46 or 48. As presently shown, the first terminal 62 is coupled to the second conductor 44 and the second terminal 64 is coupled to the first conductor 48.

The first terminal 62 is located on the second end wall 59 of the sensor 60 in line with the first lumen 44'. The second terminal 64 is also located on the second end wall 59 and is located offset from the central axis CA to effect connection with the first conductor 48 in a manner which will become apparent.

Each terminal 62 and 64 connects to associated electronic components within the sensor 60 in order to transmit the sensed physical conditions within the body to electronic signals sent to the pulse generator located remotely thereof. Each conductor to sensor terminal connection is made using a standard connection, such as, by a weld or by crimping.

As best seen in FIGS. 2 and 4, the first conductor 48 has a connection portion 70 extending axially thereof and is defined by a coiled connection section 72 which extends generally parallel to the central axis CA. The coiled connection section 72 is of an outer diameter D2 substantially less than the inner diameter D1 of the remainder of the first conductor 48. The coiled connection section 72 connects to the second terminal 64 and includes a bridging portion 76 which is a continuous length of the first conductor 48 and is directed in a manner so as to locate the coiled connection section 72 offset from the central axis CA and the remainder of the first conductor 48.

As seen in FIG. 3, each of the first and second end walls 57 and 59 of the sensor device 60 has a through opening 78 and 80 formed therein. Each such opening is generally circular in form and has a diameter which is only slightly larger in size than the outer diameter of the second conductor 46. In this way, the second conductor 46 being of a length longer than that of the conductors 44 and 48, is caused to pass through the sensor device via openings 78 and 80. As illustrated, an insulative sheathing 82 is provided around the second conductor 46 in the region where it passes through the sensor device 60 so as to protect against shorting with the terminals 62 and 64, and/or with the electronic components within the sensor device 60. The second conductor 46 is of a length sufficient to extend beyond the first end wall 57 and ultimately connects to the tip electrode 51 where it delivers a pulse for pulse control and/or defibrillation control.

By the foregoing, a multi-conductor lead body has been described by way of the illustrative sensor embodiment. However, numerous modifications and substitutions may be made to the invention without departing from the spirit of the invention. For example, while disclosed in the preferred embodiment as a three conductor lead, it is entirely within the purview of the invention to use additional conductors within additional lumens provided in the multilumen tubing 24. In addition, the invention may be used in a unipolar or bipolar mode as well as with a stimulation coil and/or pacing lead.

Accordingly, the invention has been described by way of the illustrated embodiment.

What is claimed is:

1. An implantable multi-conductor lead, comprising:
   an insulation tubing, defining a lead axis, extending between a distal end and a proximal end, the tubing containing at least a first and a second lumen therein respectively defining first and second axes, each radially displaced from the lead axis, the tubing having an outer surface defining an outer diameter thereof;
   a first conductor coiled about the outer diameter of the insulation tubing;
   a second conductor housed within the first lumen in the tubing;
   a third conductor housed within the second lumen in the tubing;
   an insulation coating disposed circumnferentially about the first conductor;
   an electrode assembly located at the distal end of the tubing and coupled to the first, second and third conductors; and
   a proximal connector assembly coupled to the first, second and third conductors at the proximal end of the tubing.

2. The implantable lead, as defined in claim 1, wherein the first conductor comprises a drawn-filled tubing.

3. An implantable multi-conductor lead, comprising:
   an insulation tubing extending between a distal end and a proximal end, the tubing containing at least a first and a second lumen therein, the tubing having an outer surface defining an outer diameter thereof;
   a first conductor coiled about the outer diameter of the insulation tubing;
   a second conductor housed within the first lumen in the tubing;
   a third conductor housed within the second lumen in the tubing;
   an insulation coating disposed circumferentially about the first conductor;
   an electrode assembly located at the distal end of the tubing and coupled to the first, second and third conductors;
   a proximal connector assembly coupled to the first, second and third conductors at the proximal end of the tubing; and wherein
   the first conductor comprises an offset portion for connection to the electrode assembly, the offset portion having a continual length of the first conductor and ending in a coil portion which has a diameter substantially less than the outer diameter of the tubing.

4. The implantable lead, as defined in claim 3, wherein the electrode assembly comprises:
   a sensor having a first terminal connected to the offset portion of the first conductor and a second terminal disposed in line with one of the second and third conductors.

5. The implantable lead, as defined in claim 4, wherein:
   the electrode assembly further comprises a distal stimulation electrode; and
   a selected one of the second and third conductors extends beneath and beyond the sensor to the distal end of the lead for electrical contact with the distal stimulation electrode.

6. The implantable lead, as defined in claim 3, wherein the electrode assembly comprises:
   a first ring electrode connected to the offset portion of the first conductor;
   a second ring electrode disposed in line with one of the second and third conductors; and
   a distal tip electrode coupled to the other of the second and third conductors.

7. A method of making an implantable multi-conductor lead, comprising the steps of:
   forming an insulation tubing defining a lead axis of desired length with at least a first and a second lumen therein respectively defining first and second axes, each radially displaced from the lead axis, the tubing having an outer surface defining an outer diameter thereof;
   attaching a first coiled conductor about the outer diameter of the insulation tubing;
   inserting a second conductor within the first lumen of the tubing;
   inserting a third conductor within the second lumen of the tubing;
   connecting an electrode assembly at the distal end of the tubing and coupling the first, second and third conductors thereto;
   connecting a proximal connector assembly to the first, second and third conductors at the proximal end of the tubing; and
   applying an insulation coating circumferentially about the first conductor.

8. The method, as defined in claim 7, further comprising the step of:
   forming the first conductor of a drawn-filled tubing.

9. A method of making an implantable multi-conductor lead, comprising the steps of:
   forming an insulation tubing of desired length with at least a first and a second lumen therein, the tubing having an outer surface defining an outer diameter thereof;
   attaching a first coiled conductor about the outer diameter of the insulation tubing;
   inserting a second conductor within the first lumen of the tubing;
   inserting a third conductor within the second lumen of the tubing;
   connecting an electrode assembly at the distal end of the tubing and coupling the first, second and third conductors thereto;
   connecting a proximal connector assembly to the first, second and third conductors at the proximal end of the tubing;
   applying an insulation coating circumferentially about the first conductor; and wherein the step of connecting the electrode assembly to the first conductor comprises the step of forming an offset portion using a continual length of the first conductor and ending in a coil portion which has a diameter substantially less than the outer diameter of the tubing.

10. The method, as defined in claim 9, wherein the electrode assembly comprises a distal stimulation electrode and a sensor having a first and a second terminal, the step of connecting the electrode assembly comprises the steps of:

connecting the first terminal of the sensor to the offset portion of the first conductor;

connecting a second terminal of the sensor with one of the second and third conductors; and connecting the other one of the second and third conductors beneath and beyond the sensor to the distal end of the lead for electrical contact with the distal stimulation electrode.

11. The method, as defined in claim 9, wherein the step of connecting the electrode assembly comprises the steps of:

connecting a first ring electrode to the offset portion of the first conductor;

connecting a second ring electrode with one of the second and third conductors; and connecting the other one of the second and third conductors to a distal stimulation electrode.

* * * * *